(12) United States Patent
Brasil

(10) Patent No.: US 8,398,942 B2
(45) Date of Patent: Mar. 19, 2013

(54) SELF-SUSTAINABLE MOBILE BIODIESEL PRODUCTION PLANT AND METHOD

(75) Inventor: Alex Nogueira Brasil, Itaúna-MG (BR)

(73) Assignee: Biominas Industria de Derivados Oleaginosos Ltda., Itauna—MG (BR)

( * ) Notice: Subject to any disclaimer, the term of this patent is extended or adjusted under 35 U.S.C. 154(b) by 134 days.

(21) Appl. No.: 12/937,614

(22) PCT Filed: Jan. 14, 2010

(86) PCT No.: PCT/BR2010/000012
§ 371 (c)(1),
(2), (4) Date: Oct. 13, 2010

(87) PCT Pub. No.: WO2010/085864
PCT Pub. Date: Aug. 5, 2010

(65) Prior Publication Data
US 2011/0167712 A1   Jul. 14, 2011

(30) Foreign Application Priority Data
Jan. 27, 2009   (BR) .................................... 0900425

(51) Int. Cl.
*B01J 8/04* (2006.01)
*B01J 8/00* (2006.01)
*B01J 19/00* (2006.01)
*C10L 1/00* (2006.01)
*C10L 1/10* (2006.01)
*C10L 1/18* (2006.01)

(52) U.S. Cl. ........ 422/630; 422/105; 422/129; 422/187; 422/600; 44/307; 44/308; 44/385; 44/388

(58) Field of Classification Search .................. 422/105, 422/129, 187, 600, 630; 44/307, 308, 385, 44/388, 629
See application file for complete search history.

(56) References Cited

U.S. PATENT DOCUMENTS

| 6,979,426 B2* | 12/2005 | Teall et al. .................... 422/237 |
| 2005/0006290 A1 | 1/2005 | Patten |
| 2005/0011112 A1* | 1/2005 | Khalil et al. .................... 44/401 |
| 2007/0240362 A1 | 10/2007 | Keady |

FOREIGN PATENT DOCUMENTS

| CN | 101134903 A | 3/2008 |
| CN | 201125231 Y | 10/2008 |

* cited by examiner

*Primary Examiner* — Walter D Griffin
*Assistant Examiner* — Natasha Young
(74) *Attorney, Agent, or Firm* — Porzio, Bromberg & Newman, P.C.

(57) ABSTRACT

The "MOBILE PLANT FOR SELF-SUSTAINABLE BIODIESEL PRODUCTION AND MOBILE PROCESS FOR BIODIESEL PRODUCTION" characterized by a compact equipment arrangement for the biodiesel production in a way intended to reduce waste generation and, additionally, allow reuse/application of some of them; it is organized and arranged over a chassis with axle and wheels that can be attached and taken to various locations, presents a self-sustainable format to use its own fuel to generate electricity to supply the entire plant, if necessary.

9 Claims, 3 Drawing Sheets

US 8,398,942 B2

SELF-SUSTAINABLE MOBILE BIODIESEL PRODUCTION PLANT AND METHOD

CROSS REFERENCE TO RELATED APPLICATION

This is a National Stage of International Application No. PCT/BR2010/000012, filed 14 Jan. 2010, which claims the benefit of Application No. PI0900425.4, filed in Brazil on 27 Jan. 2009, the disclosures of which Applications are incorporated by reference herein.

This procedure aims to provide a feasible technical way to produce biodiesel fuel from renewable sources, to meet the proposed demands of the National Program for Biodiesel Production and Use, PNPB, launched and promoted by the Brazilian Federal Government. This is a route and metric of production that provides the security demanded for the equipment operation involved, and use of products obtained.

The Mobile Biodiesel Plant, designed and developed with focus on sustainable energy, has its technical pillars secured by its own scientific research and foundations in international scientific literature.

Having energy and environmental sustainability as its primary object, the process seeks to establish a route and equipment for biodiesel production from vegetable oils in natura and/or residual, from diverse oilseeds. In order to produce biofuel of interest, it is required as an input, besides the oil chemically known as triglycerides, an alcoholic source, preferably primary short-chained and the use of an acid or basic homogeneous catalyst.

The mobile character of the production process is the main innovative parameter in accordance with the worldwide state of the technique, allied to innovation over sustainability and self-sufficiency of the unit, once it can be operated in remote areas, even without electricity supply or inputs for a certain period of time. It is noticeable, still, in terms of innovation and sustainability, the matter of application of products from the production process into some processing stages, with the goal of reducing the need for external inputs, besides producing a smaller amount of waste and reducing energy consumption.

STATE OF TECHNIQUE

There are several studies conducted on biodiesel production and processes of different routes have been described, typically making use of batch processes and, eventually, semi-continuous processes with the introduction of expensive technologies that are too complicated to operate, as the microwave or ultrasonic energy.

An example of this is the patent request U.S. 2002/0074760 A1 which describes a reaction route in which the catalyst is mixed with oil and applied to microwave energy, to force the mixture when there is an adding from the alcoholic source. It has been said that the process is not only capable of producing biodiesel, but also products from fractional distillation, as from gasoline, kerosene.

The Brazilian application PI 0404243-3 A protects a process of biodiesel production from semi-refined vegetable oil, anhydrous alcohol and alkaline catalyst in heated reaction environment that occurs in two stages. Both occur at temperatures between 60-80° C. when, after the first stage the products are sent to a heating stage to recover the unreacted alcohol by evaporation, followed by its condensation. As soon as the liquid mixture is cooled and separated into two phases, the lighter phase is a mixture of esters and oil and the denser phase is rich in glycerol. Then, the lighter phase is directed to the second reactor, where more alcohol is added according to the need for continuity of the reaction to reach an intended transformation. After that, the catalyst is neutralized with an acid additive. Alcohol in excess is eventually recovered and the phases, products from reaction, separated by decantation or centrifuge. The phase of interest, the lighter one, is washed with a mixture of water and then, strongly heated to remove water incorporated into the organic phase.

It is important to mention that the process described above has technical flaws regarding the thermodynamics of the reaction in question due to stages named after-treatment of reaction mixture, besides, some procedures used, could affect its economic viability and, later on, have an excessive dependency on external inputs of productive route.

The Brazilian work patented under the code PI0503631-3A describes a process for biodiesel production especially from castor oil, but applicable to other sources of oil in which the acidic or basic catalytic process, occurs in two stages, the first one being in two vessels in parallel and, after separating the lighter phase from the denser one, the former is directed to a second reactor where they mixture the first tow roll of tanks, for a second reaction stage. The above process highlights the reuse of the catalytic converter available in glycerin, the denser part mentioned, to reduce the emission of wastes. Another point to be highlighted is a concern about the recovery of alcohol, which must be added in excess to the reaction that occurs more quickly and efficiently. This recovery stage is performed after the separation of phases and fuel washing, produced as a purification step.

This work comes with the idea, maybe even tasteless, to reuse one of its process lines in a following stage, to take advantage of the excessive catalyst in a second of reaction, however the mentioned action may interfere considerably in kinetics reaction, once having the incorporation of a reaction product as an input vehicle. On the other hand, it starts with the idea of not mixing the dense phase, the reaction product, with the washing water, not to jeopardize its following reapplication. This organization proved to be interesting and safe in future procedural routes tested by this group and one of the reasons to develop the distinct work.

Another recent work, PI0700781-7A is about the production of biodiesel from animal fat, particularly swine, making use of methanol as a source of alcohol. However, it proves to be an inefficient process for the final quality assured to the product as well as what it refers to process timing as a whole. Unlikely, the interest process of the current work is not applied to the conversion of animal fat into biodiesel. The intended focus here may only be applied if that fat is mixed, under heating, with vegetable oil.

Very well described by the current work, registered under the code PI 0604251-1A, the vegetable oils, when extracted, either by the use of organic solvents or by pressing, carry on their composition not only triglycerides but also some organic acid content due to the presence of free fatty acids. Other possible components of these oils are substances commonly referred to as "non-saponifiable matter". Intuitively one may realize that these compounds are not converted into biodiesel when there is transesterification, it soon makes necessary the removal of this fraction in order to raise the purity of the final product: biodiesel. One of the applicable processes is named Degumming, for instance. However, some of these compounds should be kept in oil, even when not transformed, but they present some interesting characteristics to oil and to fuel such as oxidation stability, as it is the case of tocopherols and sterols. Unfortunately, removing one of the non-saponifiable compounds, all the others are removed as a consequence. This current work doesn't deal with the application of the solid part, inherent product from oilseed extraction, but explores a potential application straight in one stage of purification of biodiesel, the main product of interest.

SUMMARY OF THE INVENTION

With all the above techniques and foundation already in place, the objective of the current application is the development of a biodiesel productive route, with emphasis in a process of high technical and economic sustainability environment, added to the feature of mobility of the whole productive process. Additionally, it assumes a prominent position in the market scenario for providing a biodiesel production plant, suitable for small demands of ethanol. Linked to the mobility of the industrial process it can make available for the most remote communities, an innovative process for conversion of raw or fried vegetable oil in a power source for agricultural equipment.

The process is capable of transforming different vegetable oils just like soybean, sunflower, canola, jatropha, canola and crambe in addition to waste oils, providing the recycling. As alcoholic input it makes use of primary alcohols of low molecular weight in basic or acidic homogenous catalysis process.

Considering that:

1. PNBP, National Program of Biodiesel Production and Use, already highlights the necessity of process production in local consumption of biodiesel;
2. There are numerals oilseeds that provide oil to be transformed into biodiesel;
3. The oil sources provide considerable quantity of solid wastes, in the process of oil extraction. Those same wastes, for some oilseeds still don't have safe commercial application;
4. The purification processes for biodiesel production demand the addition of several new inputs;
5. The biodiesel production route is a potential generator of co-products. Mostly with low market application up to the present moment;
6. There is a favorable energy balance for reapplication of certain co-products before an eventual disposal.

The proposal to have a mobile unit of self-sustainable biodiesel production is to provide an innovative process, adding reengineering concepts and energy coming from waste, described as the following.

BRIEF DESCRIPTION OF THE DRAWINGS

The present invention will now be more fully described in the context of preferred features and the advantages thereof, with references to FIGS. 1 to 3 in which.

DESCRIPTION OF THE INVENTION

Figure 1:
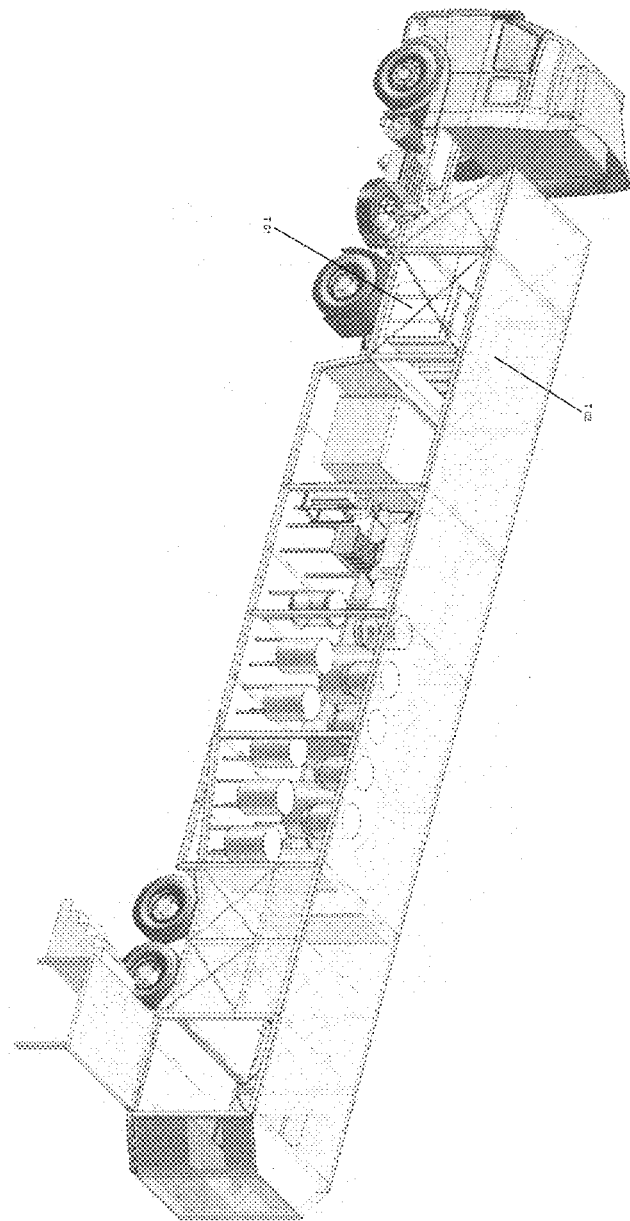
FIG. 1, hereafter picture 1, depicts the perspective view of the mobile plant for self-sustainable biodiesel production.
Figure 2:
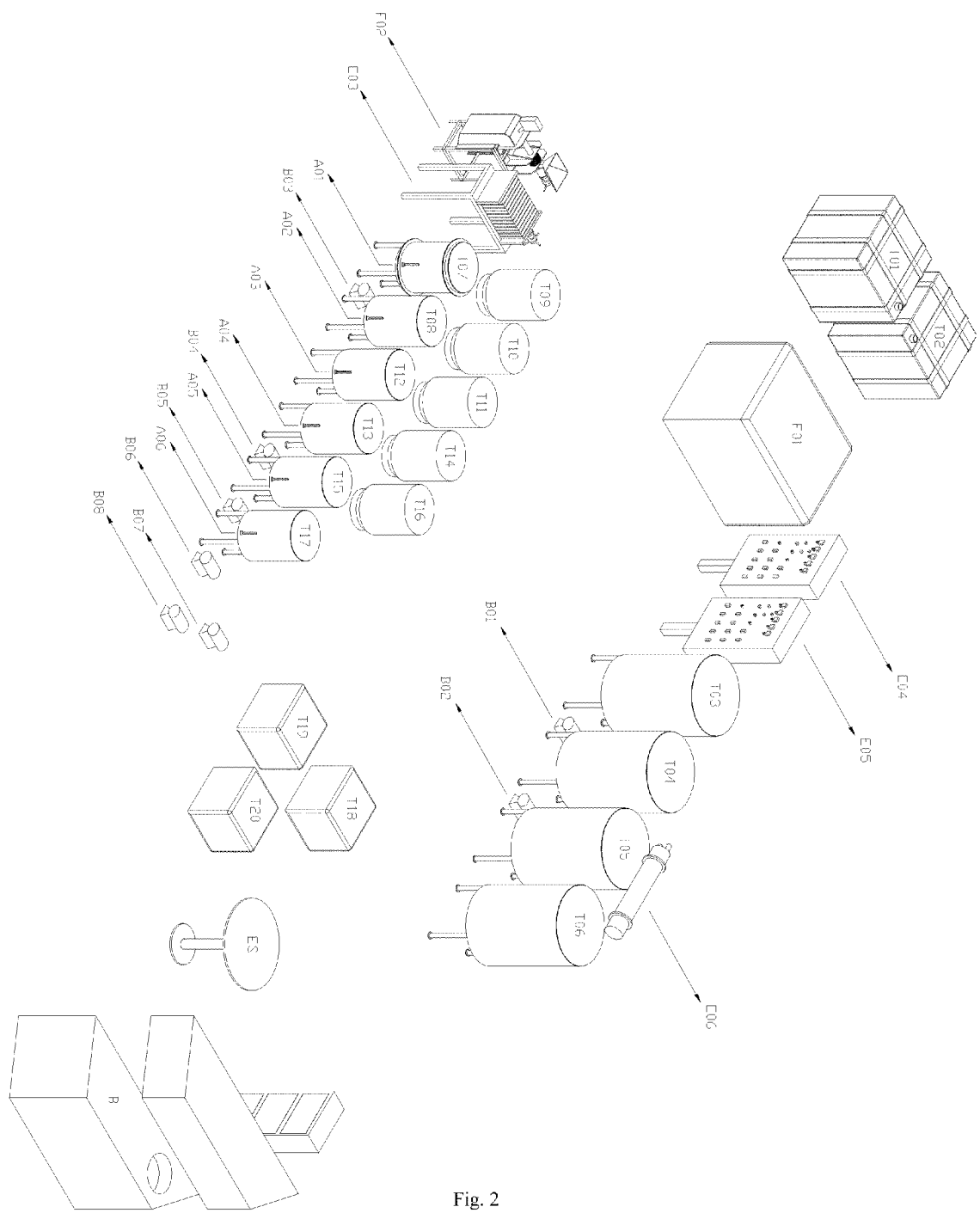
FIG. 2, hereafter picture 2, depicts the exploded view of the mobile plant for self-sustainable biodiesel production.
Figure 3:
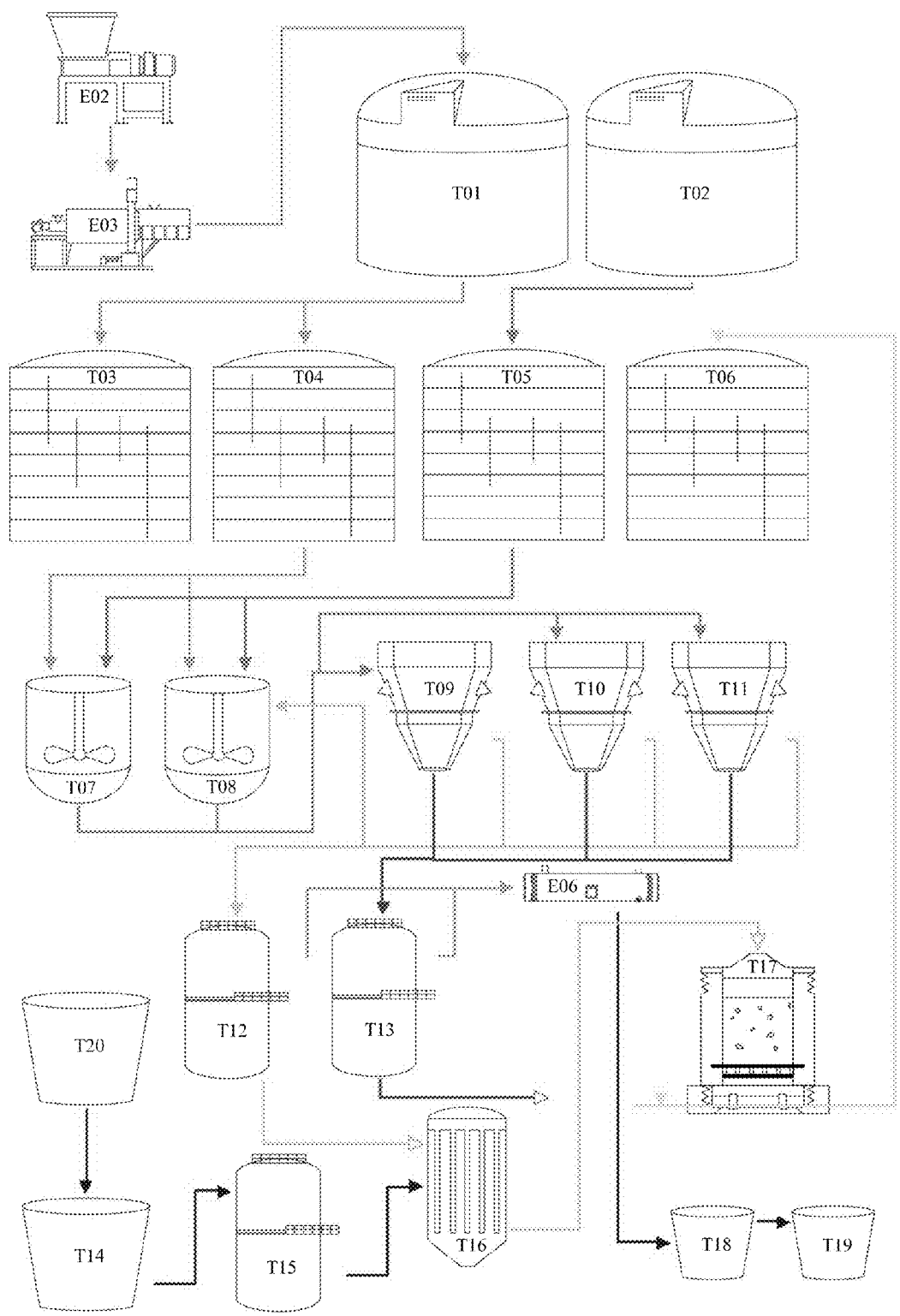
FIG. 3, hereafter picture 3, depicts the process of biodiesel production.

As an initial motivation, the mobile feature is the first and most noticeable inventive factor in question. All the productive process, since the seeds processing, pre-treatment of oil, either raw vegetable or residual, used as the route for biodiesel production, having aggregated a part of storage and tankage, was contemplated. In addition, electric power generating equipment, water tanks and process water, as well as needed infrastructure for instrumentation and equipment control, also preliminary analysis of the product in focus, the biodiesel, were aggregated to the structure. At the processing and oil reaction parts, the tanks and reactors were arranged to take the most of the vertical gap, reducing the necessity for a large number of pumps for circulation of fluid phases.

As shown in pictures 1 and 2, respectively, there are the perspective view and the exploded view of the MOBILE PLANT FOR SELF-SUSTAINABLE BIODIESEL PRODUCTION. The plant was designed and built over a movable structure, such as an articulated truck body. In this picture, the truck is being represented only in illustrative form. Over such structure, the equipment and utilities were constructed and organized. To name them:

1. 02 oil and alcohol storage containers (T01 and T02), to keep these substances during transport;
2. Power generator (E01), diesel engine which allows the application of the product that was generated at the plant as an energy source for that same engine.
3. Unit (E02) continuous extraction of vegetable oilseeds by mechanical pressing.
4. Oil filtration unit (E03), with a semi continuous operation, to remove suspended solids and container for eventual pH correction or addition of drying agent or flocculants, if necessary;
5. On the left, (E04 and E05) electric control equipment panels;
6. Besides 04 tanks made of stainless steel, for storage and oil supply in natura (T03), residual (T04) alcohol tanking (T05) and at last biodiesel storage (T06) already produced and polished;
7. At the middle right, the reactors and processing utilities from front to rear, all made of stainless steel. To name them:
   7.1 First reactor (T07) with heating (A01) and temperature control between ambient temperature and 80° C., besides agitation controlled by frequency converter limited between 450 and 1000 rpm;
   7.2 First Settling tank (T09)
   7.3 Second reactor (T08), the same as item 7.1, with heating (A02) and agitation controlled;
   7.4 Second Settling tank (T10)
   7.5 Storage (T12) of the dense phase, glycerin, with heating (A03) limited to 100° C. with outlets for liquids at the base and for gases at the top,
   7.6 Third Settling tank (T11)
   7.7 Purification tank (T13) of the esters mixture and as the storage tank at 7.5, with controlled heating (A04) and with outlets for liquids at the base, and for gases at the top;
   7.8 Heat exchanger (E06) of tubes operated in countercurrent;
   7.9 Clean water passage box (T14)
   7.10 (T15) Heating storage of clean water for the process, with a limit of 80° C. in temperature rising;
   7.11 liquid-liquid extraction column (T16) for removing water soluble impurities from biodiesel;
   7.12 Drying column (T17), with heating (A06) controlled between ambient temperature and 100° C., besides vacuum system (B08) controlled from ambient pressure to 100 mmHg, for final biodiesel polishing;
8. Office (ES) for organization and laboratory work;
9. Cabinets and laboratories of physic-chemical analysis of the primary product.

The entire set is equipped with lighting system, emergency exits and fire extinguishers suitable for the structure in question. The process of biodiesel production represents in picture 03:

Flowchart of the mobile process for biodiesel production designed and built over a mobile handset.

In the beginning of the production process from the oilseed, that same seed is mechanically pressed (E02) for vegetable oil extraction, resulting in a vegetable oil with high solid contents, and a pie, solid part with low oil remaining. In the next stage, the oil is filtered (E03) and if necessary has its pH corrected before reaching the mobile-power-pump (B07). From this stage the oil can go to the tank (T01) of vegetable oil in natura storage. Eventually when processing residual oil, it has the beginning of its process with the filtration (E03) and in sequence it is directed to tanking (T02). Later, the oil is powered by pumping (B01) in one of the reactors (T07 or T08), that work in parallel, and may, if needed, undergo a process of pre-treatment or refining, in the first reactor (T07) for the removal of chemical components that are not wanted in the final product. Then it goes to a decantation stage (T09) of the phases, the lighter one being the one of interest. The oil, eventually well treated, follows to the second reactor (T08) in which alcohol will be added by pumping (B020), under heating (A02) and strong agitation to force the mixing of the two phases. As soon as the catalyst is added and, under the control of temperature, its reaction is developed.

Once the inputs react, biodiesel and glycerin are produced, and must be split. Due to considerable density differences, the process can be performed by decantation (T09, T10 or T11), with gravity aid, searching for energy and space economy.

The phases are split in different tanks. The light fraction, fatty esters, is directed to the purification tank (T13), and the heavy fraction, rich in glycerin and alcohol is directed to the storage (T12) of the dense phase. An independent heating system (A03 and A04) is activated for alcohol evaporation that is prominent from the excess of the reaction phase, to increase the efficiency and reaction kinetics. Under heating, the alcohol is evaporated in: dense phase storage (T12) and purification tank (T13) and subsequently condensed in the heat exchanger (E06) of parallel tools in countercurrent to liquid cooling. Alcohol returns to its original tank ready for further application in the next process without waste generation at that stage.

For co-solubility, a small fraction of glycerin was transported during the lighter phase due to the alcohol that was solubilized and that once was just removed by evaporation. The removal of that small impurity fraction in a process of liquid-liquid extraction (T16) soon becomes simple, having oil as its stationary phase; heated water is added to the column, that suffuses the organic lighter phase.

For not mixing, the organic ester phase and the water split by Settling tank (T16), the water set aside for the biodiesel (still under purification). Once they are split, the water is stocked (T18 and T19) for post application. The biodiesel with a small incorporated humidity is directed to a drying column (T17) where, with heating and pressure reduction by an operation vacuum pump (B08), the water is withdrawn and released as vapor into the environment. The biodiesel, dry, is ready for tanking (T06) and use as fuel, applied pure or in fractions of a mixture with mineral diesel.

An innovation proposed on the described route refers to the application of glycerin (retained in T12) as an additive on the coolant heat exchanger (E06). The glycerin, that initially has no direct application on the process, starts working as a heat transfer material, to condense evaporated alcohol in (T12) and (T13) returning the same to alcohol storage tank (T05). As the glycerin is completely soluble in water it can be solubilized in this one and exchange heat from alcohol vapor.

This organization and arrangement provides a relative compact industrial structure achieving a high level of operation performance and efficiency. It is added to the security, already mentioned, and durability of the plant, due to damping systems and connections developed, reducing the strictness of the system, warning about the appearance of cracks and wear out of equipment due to the unit transport. Once assembled, the equipments are perfectly integrated with components connected by flexible joints and flanges. Therefore, the mobile plant, despite having a small size for a plant, puts itself into an inventive character of an innovative model of production able of reaching diverse locations with safety, durability and quality in the processing system.

EXAMPLE 1

Cold pressed oilseeds are received (E02) for mechanical extraction of vegetable oil in natura and thrown into the filter press (E03) from which tanking pumps follow (T03). 100 kg of oil for reactor (T07) is directed for pumping (B01) where it is heated under 55° C. and mixed in 31 kg alcohol, directed by pump (B02), from its tank (T05), and 4.5 kg of catalyst added manually. Under strong agitation, the mixture remains for 45 minutes. It is directed by pump (B03) to separation phases (T11) where it is kept it remains in rest for one hour and from there directs the inferior phase by gravity to glycerin tanking (T12) and the lighter phase to purification (T13) where the excess of alcohol will be evaporated by heating (A03 and A04) under 75° C. for 40 minutes. The retained material in tank is directed, by pump (B04), to washing (T16) where it is pulverized by pumping (B05), heated water (T15) at 50° C. and remains for phase separation for 30 minutes. The tanking water and the lighter phase for drying (T17) at 100° C. and at 0.80 atm of pressure for 25 minutes. The biofuel, ready for tanking is directed by pumping (B06).

EXAMPLE 2

Frying oil is received and thrown into the filter press (E03) from which follows by pumping (B01) for tanking (T04). 100 kg of oil for the reactor is directed by pump, (T07) where it is heated (A01) at 60° C. and mixed with 35 kg alcohol, directed by pump (B02) from its tank (T05), and 5 kg of catalyst added manually. Under strong agitation, the mixture continues for 15 minutes. 100 kg of oil are directed to reactor (T07) where it is heated (A01) ate 60° C. and mixed with 35 kg of alcohol directed by pump (B02) from its tank (T05) and 5 kg of catalyst, directs by pump (B03) for phases separation (T09) where it is kept in rest for an hour and from there directed by gravity the inferior phase for 30 minutes. It is directed by gravity the water for tanking (T18) and the lighter phase for drying (T17) at 100° C. and at 0.90 atm of pressure for 30 minutes. It is directed by pumping (B06) the biofuel ready for tanking (T06).

The invention claimed is:

1. A mobile plant for self-sustainable biodiesel production of configuration and arrangement of components on a rigid frame, chassis, on wheels, with one or two axels, comprising a vegetable oil storage container; a methanol or ethanol storage container; an electric generator with diesel engine; a unit of oil extraction by mechanical pressing; a filtration unit for vegetable recycling oils or in natura oils, optionally a stage to correct the pH of the oil; electrical control panel for starting and stopping of energy of all electrical system of motors, pumps and heating; electrical panel to activate lighting and electrical supply outlets an in natura vegetable oil storage container for storing vegetable oils from a process of mechanical pressing of oilseeds, followed by filtration; storage container for waste vegetable oil; a storage container for alcohol, the alcohol containing up to eight carbon atoms in its structure; storage container for biodiesel produced and purified; first reactor with controlled stirring and heating for the refining reactions or transesterification of vegetable oil; optionally a second reactor with controlled stifling and heating; a first settling tank for phase separation of refining or transesterification of vegetable oil, biodiesel or just reacted; a second settling tank operated in parallel to the first settling tank; a third settling tank operated in parallel to a first storage container of the dense phase produced in the transesterification reaction and separated; the first settling tank, the second settling tank or the third settling tank with heating to recover the methanol or ethanol; a second storage tank using heating to recover the unreacted methanol or ethanol in the transesterification step; heat exchanger for condensing the vapor of methanol or ethanol produced at the first storage container and the second storage container; a cold water container;

a hot water tank with heating controlled to provide hot water to the process of purifying biodiesel; a liquid-liquid extraction column for hot washing the biodiesel produced under the polishing process; a drying tower of washed biodiesel with controlled heating, reduced pressure and circulation system and pumping of the processed liquid; a storage container of clean water for powering plant and laboratory; containment box of water from the process, coming from the stage of glycerin extraction from biodiesel into the liquid-liquid extraction column or from coolant liquid in the heat exchanger; and a box to contain the overflow of the containment box, while full loaded.

2. The mobile plant for biodiesel production according to claim 1, further comprising:

a first mobile pump for connecting the vegetable oil storage container to the in natura vegetable oil storage container and the storage container for waste vegetable oil, and optionally the methanol or ethanol storage container to the container for alcohol;

the first mobile pump for connection of filtered oil in the filtration unit to the in natura vegetable oil storage container or the storage container for waste vegetable oil tank as source of oil; the mobile plant operated by the steps of:

a) pumping, with the first pump, vegetable oil in the in natura vegetable oil storage container tanks and/or in natura vegetable oil in the storage container for waste vegetable oil up to the first reactor and/or the second reactor;

b) pumping with a second pump, alcohol from a storage container for alcohol tank to the first reactor and/or the second reactor;

c) executing a reaction in the first reactor and/or the second reactor with heating, and/or, forced mechanical agitation;

d) pumping the reaction mixture from the first reactor and/or the second reactor to the first settling tank, the second settling tank, or the third settling tank;

e) directing the light phase, fatty esters, by gravity to a next stage the second storage tank;

f) directing by gravity, the denser phase, rich in glycerin, to the first storage tank;

g) evaporation of excessive alcohol by heating, simultaneously or otherwise, the first storage tank or the second storage tank, as a step for reducing waste production, alcohol recovery and raising the purity level of the product and biodiesel co-product glycerin;

h) directing esters from the second storage tank by pumping for polishing on a wet hot passage in the liquid-liquid extraction column;

i) directing cold water from the process from the cold water container to a hot water container, by gravity to provide hot water to the process of purifying biodiesel;

j) directing by pumping water from hot process to the liquid-liquid extraction column where it is sprayed;

k) decantation in a dense phase in the liquid-liquid extraction column, wash water, directed by gravity to the containment box;

l) directing a light phase, organic, by gravity to the last purification step in a drying tower of washed biodiesel; and m) drying of biodiesel in the drying tower with controlled heating drop in pressure and liquid circulation by pumping.

3. The mobile plant for biodiesel production of claim 2, wherein methanol or ethanol added in excess to run the reaction at the first reactor and/or the second reactor, are recovered with the use of heating in the first storage tank and/or the second storage tank.

4. The mobile plant for biodiesel production of claim 2, wherein there is a direct connection by gravity of the water in the cold water container and the hot water container.

5. The mobile plant for self-sustainable biodiesel production as in claim 1, wherein the vegetable oil storage container and the methanol or ethanol storage container are arranged over a second wheel of the mobile chassis.

6. The mobile plant for self-sustainable biodiesel production as in claim 1, may comprise an office for management process, structured with telephony and mobile internet; laboratory for preliminary testing of oils for processing and for the qualitative physico-chemical processing and analysis of the quality of inputs and products involved in the mobile biodiesel plant operation.

7. The mobile plant for self-sustainable biodiesel production as in claim 6, further comprising fire extinguishers and/or roof structure and lighting system.

8. A method of using a mobile plant for self-sustainable biodiesel production of configuration and arrangement of components on a rigid frame, chassis, on wheels, with one or two axels, comprising a vegetable oil storage container; a methanol or ethanol storage container; an electric generator with diesel engine; a unit of oil extraction by mechanical pressing; a filtration unit for vegetable recycling oils or in natura oils, optionally a stage to correct the pH of the oil; electrical control panel for starting and stopping of energy of all electrical system of motors, pumps and heating; electrical panel to activate lighting and electrical supply outlets; an in natura vegetable oil storage container for storing vegetable oils from a process of mechanical pressing of oilseeds, followed by filtration; storage container for waste vegetable oil; a storage container for alcohol, the alcohol containing up to eight carbon atoms in its structure; storage container for biodiesel produced and purified; first reactor with controlled stirring and heating for the refining reactions or transesterification of vegetable oil; optionally a second reactor with controlled stirring and heating; a first settling tank for phase separation of refining or transesterification of vegetable oil, biodiesel or just reacted; a second settling tank operated in parallel to the first settling tank; a third settling tank operated in parallel to a first storage container of the dense phase produced in the transesterification reaction and separated; the first settling tank, the second settling tank or the third settling tank with heating to recover the methanol or ethanol; a second storage tank using heating to recover the unreacted methanol or ethanol in the transesterification step; heat exchanger for condensing the vapor of methanol or ethanol produced at the first storage container and the second storage container; a cold water container; a hot water tank with heating controlled to provide hot water to the process of purifying biodiesel; a liquid-liquid extraction column for hot washing the biodiesel produced under the polishing process; a drying tower of washed biodiesel with controlled heating, reduced pressure and circulation system and pumping of the processed liquid; a storage container of clean water for powering plant and laboratory; containment box of water from the process, coming from the stage of glycerin extraction from biodiesel into the liquid-liquid extraction column or from coolant liquid in the heat exchanger; and a box to contain the overflow of the containment box, while full loaded, comprising the step of: simultaneously reacting the raw vegetable from the vegetable oil storage container or the in natura oils from the in natura vegetable oil storage container with different oils, storage and split power supply from two the sources of vegetable oils in the first reactor and the second reactor.

9. A method of using a mobile plant for self-sustainable biodiesel production of configuration and arrangement of components on a rigid frame, chassis, on wheels, with one or two axels, comprising a vegetable oil storage container: a methanol or ethanol storage container: an electric generator with diesel engine; a unit of oil extraction by mechanical pressing; a filtration unit for vegetable recycling oils or in natura oils, optionally a stage to correct the pH of the oil; electrical control panel for starting and stopping of energy of all electrical system of motors, pumps and heating; electrical panel to activate lighting and electrical supply outlets; an in natura vegetable oil storage container for storing vegetable oils from a process of mechanical pressing of oilseeds, followed by filtration; storage container for waste vegetable oil; a storage container for alcohol, the alcohol containing up to eight carbon atoms in its structure; storage container for biodiesel produced and purified; first reactor with controlled stirring and heating for the refining reactions or transesterification of vegetable oil; optionally a second reactor with controlled stirring and heating; a first settling tank for phase separation of refining or transesterification of vegetable oil, biodiesel or just reacted; a second settling tank operated in parallel to the first settling tank; a third settling tank operated in parallel to a first storage container of the dense phase produced in the transesterification reaction and separated; the first settling tank, the second settling tank or the third settling tank with heating to recover the methanol or ethanol; a second storage tank using heating to recover the unreacted methanol or ethanol in the transesterification step; heat exchanger for condensing the vapor of methanol or ethanol produced at the first storage container and the second storage container; a cold water container; a hot water tank with heating controlled to provide hot water to the process of purifying biodiesel; a liquid-liquid extraction column for hot washing the biodiesel produced under the polishing process; a drying tower of washed biodiesel with controlled heating, reduced pressure and circulation system and pumping of the processed liquid; a storage container of clean water for powering plant and laboratory; containment box of water from the process, coming from the stage of glycerin extraction from biodiesel into the liquid-liquid extraction column or from coolant liquid in the heat exchanger; and a box to contain the overflow of the containment box, while full loaded, comprising the step of: providing clean water from the storage container of clean water to replenish and maintain the operation of the productive process.

\* \* \* \* \*